United States Patent [19]
Andreas et al.

[11] Patent Number: 5,921,994
[45] Date of Patent: *Jul. 13, 1999

[54] LOW PROFILE INTRALUMINAL SUTURING DEVICE AND METHOD

[75] Inventors: Bernard H. Andreas, Fremont; Timothy J. Wood, Los Gatos, both of Calif.

[73] Assignee: Perclose, Inc., Menlo Park, Calif.

[ * ] Notice: This patent is subject to a terminal disclaimer.

[21] Appl. No.: 08/946,206

[22] Filed: Oct. 7, 1997

Related U.S. Application Data

[63] Continuation of application No. 08/491,496, Jun. 15, 1995.

[51] Int. Cl.$^6$ ................................................ A61B 17/04
[52] U.S. Cl. ........................ 606/144; 606/139; 606/148; 112/169
[58] Field of Search .................................. 606/139, 144, 606/145, 148, 213; 604/96, 164, 264, 280

[56] References Cited

U.S. PATENT DOCUMENTS

| | | |
|---|---|---|
| 312,408 | 2/1885 | Wackerhagen . |
| 659,422 | 10/1900 | Shidler . |
| 2,646,045 | 7/1953 | Priestley . |
| 2,959,172 | 11/1960 | Held . |
| 3,470,875 | 10/1969 | Johnson . |
| 3,665,926 | 5/1972 | Flores . |
| 3,696,247 | 10/1972 | McIntosh et al. ............... 250/83.3 H |
| 3,860,344 | 1/1975 | Garfunkel .................. 356/51 |
| 3,939,820 | 2/1976 | Grayzel . |
| 3,973,118 | 8/1976 | LaMontagne ................ 250/226 |
| 3,976,883 | 8/1976 | Krakow ................... 250/343 |
| 4,157,470 | 6/1979 | Kotaka et al. ............ 250/345 |
| 4,158,772 | 6/1979 | Reedy ...................... 250/338 |
| 4,161,951 | 7/1979 | Scanlan, Jr. . |
| 4,180,734 | 12/1979 | Gedeon ..................... 250/345 |
| 4,200,791 | 4/1980 | Burough .................... 250/343 |
| 4,317,445 | 3/1982 | Robinson ................. 128/214.4 |
| 4,467,203 | 8/1984 | Rappaport .................. 250/343 |
| 4,493,323 | 1/1985 | Albright et al. . |
| 4,553,543 | 11/1985 | Amarasinghe . |
| 4,587,969 | 5/1986 | Gillis . |
| 4,694,173 | 9/1987 | Wong ....................... 250/343 |
| 4,744,364 | 5/1988 | Kensey . |
| 4,824,435 | 4/1989 | Giesy et al. ................. 604/49 |

(List continued on next page.)

FOREIGN PATENT DOCUMENTS

| | | |
|---|---|---|
| 140557 | 5/1985 | European Pat. Off. . |
| 589426 A1 | 3/1994 | European Pat. Off. . |
| 634141 A1 | 1/1995 | European Pat. Off. . |
| 647430 A2 | 4/1995 | European Pat. Off. . |
| 4210724 C1 | 7/1993 | Germany . |
| 9217932 | 7/1993 | Germany . |
| 1093-329-A | 5/1984 | U.S.S.R. . |
| 1174-036-A | 8/1985 | U.S.S.R. . |
| WO94/05213 | 3/1994 | WIPO . |
| 96/05772 | 2/1996 | WIPO . |

OTHER PUBLICATIONS

Richardson, et al., "A Novel Infrared Spectrometer Using a Linear Array Detector", Applied Spectroscopy, vol. 44, No. 5, 1990, pp. 822–882.

Maris et al., "Nonlinear Multicomponent Analysis by Infrared Spectrophotometry," Anal. Chem., 1983.

"Innovation through Progress", *Rema–Medizintechnik*, Gmbh, Jan. 1992.

Informational Letter, Datascopecorp., Montvale, NJ.

Ad: The Laurus In–Line Endoscopic Suturing Device (The Laurus ND–2600 Needle Driver), Laurus Medical Corporation, Rev. Oct. 1994.

*Primary Examiner*—Gary Jackson
*Attorney, Agent, or Firm*—Townsend and Townsend and Crew

[57] ABSTRACT

An improved suturing device and method is provided. The suturing device is of the type including a guide body and means on the guide body for translating at least one needle relative to the guide body. The suturing device is improved by providing a rotatable sleeve disposed over at least a distal portion of the guide body to facilitate introduction of the device to a puncture site.

27 Claims, 12 Drawing Sheets

U.S. PATENT DOCUMENTS

| | | | |
|---|---|---|---|
| 4,852,568 | 8/1989 | Kensey. | |
| 4,888,484 | 12/1989 | Harvey | 250/343 |
| 4,890,612 | 1/1990 | Kensey | 606/213 |
| 4,928,015 | 5/1990 | Butler et al. | 250/343 |
| 4,929,246 | 5/1990 | Sinofsky | 606/8 |
| 4,957,371 | 9/1990 | Pellicori et al. | 356/419 |
| 5,021,059 | 6/1991 | Kensey et al. | 606/213 |
| 5,046,018 | 9/1991 | Flewelling et al. | 364/497 |
| 5,061,274 | 10/1991 | Kensey | 606/213 |
| 5,092,342 | 3/1992 | Hattendorff et al. | 128/719 |
| 5,159,199 | 10/1992 | LaBaw | 250/339 |
| 5,160,339 | 11/1992 | Chen et al. | 606/158 |
| 5,171,251 | 12/1992 | Bregen et al. | 606/151 |
| 5,192,302 | 3/1993 | Kensey et al. | 606/213 |
| 5,222,974 | 6/1993 | Kensey et al. | 606/213 |
| 5,296,706 | 3/1994 | Braig et al. | 250/339 |
| 5,304,184 | 4/1994 | Hathaway et al. | 606/144 |
| 5,306,254 | 4/1994 | Nash et al. | 604/168 |
| 5,360,004 | 11/1994 | Purdy et al. | 128/633 |
| 5,379,764 | 1/1995 | Barnes et al. | 128/633 |
| 5,395,332 | 3/1995 | Ressemann et al. | 604/96 |
| 5,417,699 | 5/1995 | Klein et al. | 604/144 |
| 5,440,143 | 8/1995 | Carangelo et al. | 250/573 |
| 5,454,822 | 10/1995 | Schob et al. | 604/148 |
| 5,460,177 | 10/1995 | Purdy et al. | 128/633 |
| 5,527,321 | 6/1996 | Hinchliffe | 606/144 |
| 5,531,700 | 7/1996 | Moore et al. | 604/164 |

LOW PROFILE INTRALUMINAL SUTURING DEVICE AND METHOD

This is a Continuation of application No. 08/491,496 filed Jun. 15, 1995 still pending, the disclosure of which is incorporated by reference.

BACKGROUND OF THE INVENTION

1. Field of the Invention

The present invention relates generally to apparatus and methods for the percutaneous closure of body lumens. More particularly, the present invention relates to apparatus and methods for the percutaneous closure of arterial and venous puncture sites, which are usually accessible only through a tissue tract.

A number of diagnostic and interventional vascular procedures are now performed transluminally, where a catheter is introduced to the vascular system at a convenient access location and guided through the vascular system to a target location using established techniques. Such procedures require vascular access which is usually established using the well known Seldinger technique, as described, for example, in William Grossman's "Cardiac Catheterization and Angiography," 3rd Ed., Lea and Febiger, Philadelphia, 1986, incorporated herein by reference.

When vascular access is no longer required, the introducer sheath must be removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time-consuming, frequently requiring one-half hour or more of compression before hemostasis is assured. Additionally, such compression techniques require clot formulation and therefore cannot begin until anticoagulants used in vascular therapy procedures (such as for heart attacks, stent deployment, non-optimal PTCA results, and the like) are allowed to wear off. This can take up to two to four hours, thereby increasing the time required under the compression technique. The compression procedure is further uncomfortable for the patient and frequently requires administering analgesics to be tolerable. Moreover, the application of excessive pressure can at times totally occlude the underlying blood vessel, resulting in ischemia and/or thrombosis. Following manual compression the patient is required to remain recumbent for at least four and at times longer than 12 hours under close observation to assure continued hemostasis. During this time renewed bleeding may occur resulting in bleeding through the tract, hematoma and/or pseudo aneurysm formation as well as arteriovenous fistula formation. These complications may require blood transfusion and/or surgical intervention. The incidence of these complications increases when the sheath size is increased and when the patient is anticoagulated. It is clear that the standard technique for arterial closure can be risky, and is expensive and onerous to the patient. While the risk of such conditions can be reduced by using highly trained individuals, such use is both expensive and inefficient.

To overcome the problems associated with manual compression, the use of bioabsorbable fasteners to stop bleeding has been proposed by several groups. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel, and locating the fastener too far from that surface can result in failure to provide hemostasis and subsequent hematoma and/or pseudo aneurysm formation. Conversely, if the fastener intrudes into the arterial lumen, intravascular clots and/or collagen pieces with thrombus attached can form and embolies downstream causing vascular occlusion. Also, thrombus formation on the surface of a fastener protruding into the lumen can cause a stenosis which can obstruct normal blood flow. Other possible complications include infection as well as adverse reactions to the collagen implant.

A more effective approach for vascular closure has been proposed in U.S. Pat. No. 5,417,699 and in co-pending application Ser. Nos. 08/148,809 and PCT/US93/11864. A suture applying device is introduced through the tissue tract with a distal end of the device located at the vascular punctures. One or more needles in the device are then used to draw suture through the blood vessel wall on opposite sides of the punctures, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is important that the needles be properly directed through the blood vessel wall so that the suture is well anchored in tissue to provide for tight closure. It is also important that needle deployment within the suturing device be controlled to prevent accidental deployment before the device has been properly introduced to the puncture site in a blood vessel. It is of further importance that the vascular suturing device be able to be introduced to blood vessels without imposing significant or undue trauma to the patient. In particular, it is particularly desirable to close the vessel in a relatively short amount of time and without imposing excessive injury to the tissue tract leading to the vessel.

For these reasons, it would be desirable to provide apparatus, systems, and methods for suturing vascular punctures which meet all or some of the criteria discussed above.

2. Description of the Background Art

Devices capable of delivering pairs of needles to various tissue locations are described in the following patents and patent applications: U.S. Pat. Nos. 4,493,323 and 659,422; European patent application 140 557; and U.S.S.R. patent applications 1174-036-A and 1093-329-A. A suturing device that carries a pair of needles having suture therebetween is described in a brochure entitled "Innovation through Progress," *REMA-MEDIZINTECHNIK*, Gmbh, January, 1992. A suturing device having a partially flared cylindrical core for delivering needles to suture anastomoses is described in U.S. Pat. No. 4,553,543. Other suturing and ligating devices are described in U.S. Pat. Nos. 5,171,251; 5,160,339; 4,317,445; 4,161,951; 3,665,926; 2,959,172; 2,646,045; and 312,408. Devices for sealing percutaneous vascular punctures using various plugs and fastener structures are described in U.S. Pat. Nos. 5,222,974; 5,192,302; 5,061,274; 5,021,059; 4,929,246; 4,890,612; 4,852,568; 4,744,364; 4,587,969; and 3,939,820. Collagen fastener sealing devices are under commercial development by Datascope Corp., Montvale, N.J., and Kensey Nash Corporation, Exton, Pa. Copending application Ser. No. 08/148,809, describes a vascular suturing device having a needle guide with a constant peripheral dimension.

SUMMARY OF THE INVENTION

The present invention provides improved apparatus, systems, and methods for suturing percutaneous luminal puncture sites, particularly vascular puncture sites located at the distal end of a percutaneous tissue tract. The improvements are most applicable to paired-needle suturing systems, such as those described in U.S. Pat. No. 5,417,699 and in co-pending application Ser. No. PCT/US93/11864, and particularly for the suturing system described in co-pending application Ser. No. 08/252,124, filed Jun. 1, 1994. The disclosures of all these references are herein incorporated by reference. At least some of the improvements, however, will be equally applicable to single-needle suturing systems, such as those described in co-pending application Ser. No. 08/148,809, the disclosure of which is herein incorporated by reference, as well as other types of suturing devices known and described in the medical and patent literature.

In one particular aspect, the present invention provides an improved suturing device of the type including a guide body and means on the guide body for translating at least one needle relative to the guide body. Such a suturing device is improved by providing a rotatable sleeve disposed over at least a distal portion of the guide body. The rotatable sleeve will usually comprise a rigid cylinder having a length in the range from 30 mm to 200 mm and a diameter in the range from 3 mm to 15 mm. Such a sleeve is particularly advantageous in facilitating introduction of the suturing device to the puncture site and eliminates the need for a predilator.

In another aspect, the suturing device is further provided with a flexible tube extending distally from the guide body. The flexible tube includes a proximal end, a distal end, and a guide wire lumen extending proximally from the distal end and terminating in an exit port between the proximal and distal ends. Such a guide wire exit port is particularly useful in allowing the suturing device to be introduced into the blood vessel over a guide wire in a "monorail" fashion (i.e. with the guide wire exiting somewhere along the length of the suturing device and then running along the outside of the remainder of the device). In this way, the profile of the guide body may be kept minimal to reduce the overall size of the device. Further, such a configuration allows the guide wire to be removed from the vessel prior introduction of the guide body into the tissue tract. Preferably, the flexible tube has a length in the range from about 20 cm to 40 cm, and the exit port is located at about 5 cm to 20 cm from the proximal end. In a further aspect, the flexible tube has an outside diameter in the range from about 2 mm to 10 mm. In yet another aspect, the flexible tube includes a central lumen extending distally from the proximal end for housing the needle during insertion of the suturing device.

In a further aspect, the suturing device will preferably include a means for selectively preventing rotation of the sleeve relative to the guide body. In an exemplary embodiment, the preventing means will comprise a handle attached to the guide body, with the handle having at least one detent for engaging a groove in the sleeve. In still another aspect, at least one blood detection lumen that passes through the guide body is provided and is used in positioning the suturing device within the blood vessel. In a particularly preferable aspect, a suture lumen is further provided in addition to the blood detection lumen. The suture lumen passes through the guide body and stores at least part of a length of suture during insertion of the suturing device. Optionally, the suture lumen may also function as a blood detection lumen so that the device is provided with a second or "back-up" blood detection lumen.

The invention further provides an improved suturing device of the type including a guide body and means on the guide body for translating at least one needle relative to the guide body. The improvement comprises a flexible tube having a proximal end connected to the guide body, a distal end, and a guide wire exit port between the proximal end and the distal end. The flexible tube preferably has a length in the range from about 20 cm to 40 cm, with the exit port being located at about 5 cm to 20 cm from the proximal end. In another aspect, the flexible tube has an outside diameter in the range from about 2 mm to 10 mm. In a further aspect, the flexible tube includes means for directing a proximally advanced guide wire through the exit port.

In a particularly preferable aspect, the suturing device further includes a sleeve rotatably disposed about the guide body. The rotatable sleeve is preferably a rigid cylinder having a length in the range from 30 mm to 200 mm and a diameter in the range from 3 mm to 15 mm. In another aspect, a means is provided for selectively preventing rotation of the sleeve. An exemplary preventing means comprises a handle attached to the guide body, with the handle having at least one detent for engaging a groove in the sleeve. In still a further aspect, at least one blood detection lumen passing through the guide body is provided. A separate suture lumen may also be provided to house a length of suture. In this manner, improved suture management is provided to facilitate easier reciprocation of the needles through the suturing device when closing the vessel.

The invention provides an exemplary suturing device comprising a guide body having a proximal end, a distal end, and an internal lumen. A needle guide is provided having a proximal end attached to the distal end of the guide body and a distal end having at least two needle guide channels. A pair of needles are provided along with a length of suture having two ends, with each end attached to one of the needles and with at least a portion of the remaining length of suture passing through the internal lumen of the guide body. A shaft is provided and is reciprocatably mounted within the guide body. The shaft carries the needles and allows the needles to be reciprocated within the needle guide channels.

In one particular aspect, the suturing device further includes a pair of receiving channels in the guide body which are arranged so that reciprocation of the shaft draws the needles into the receiving channels and draws the length of suture from the internal lumen. In this way, the length of suture may be stored both within the guide body and outside the patient until the needles are reciprocated to close the vessel. In a preferable aspect, the suturing device will further include a blood detection lumen passing through the guide body. The blood detection lumen will preferably be employed in positioning the suturing device within the vessel. Optionally, the internal lumen having the length of suture may also function as a blood detection lumen so that the suturing device will be provided with a "back-up" detection lumen in the event that the blood detection lumen (without the length of suture) becomes clogged or otherwise non-operational.

In another aspect, the suturing device includes a sleeve that is rotatably disposed about the guide body. The sleeve is preferably a rigid cylinder having a length in the range from 30 mm to 200 mm and a diameter in the range from 3 mm to 15 mm. In a further aspect, a means is provided for selectively preventing rotation of the sleeve. In still a further aspect, the preventing means comprises a handle attached to the guide body, with the handle having at least one detent for engaging a groove in the sleeve. In one particularly preferable aspect, a means is provided for releasably securing the shaft to the guide body to prevent relative axial movement. In this way, needle deployment may be prevented during introduction of the suturing device to the puncture site.

In yet another aspect, the suturing device includes a flexible tube having a proximal end connected to the needle guide, a distal end, and a guide wire exit port between the proximal end and the distal end. The flexible tube preferably has a length in the range from about 20 cm to 40 cm, and the exit port is located at about 5 cm to 20 cm from the proximal end. In still a further aspect, the flexible tube has an outside diameter in the range from about 2 mm to 10 mm. In yet another aspect, the flexible tube includes means for directing a proximally advanced guide wire through the exit port.

The invention provides an exemplary method for suturing a puncture site in a blood vessel wall disposed at the distal end of a percutaneous tissue tract. According to the method, a suturing device is provided having a guide body, a sleeve rotatably disposed about the guide body, and a distally extending flexible tube. The suturing device is introduced to the puncture site so that the guide body lies within the tissue tract and the flexible tube lies within the blood vessel lumen. During insertion of the guide body into the tissue tract, the sleeve is rotated to facilitate introduction. Once positioned at the puncture site, a needle carrying a length of suture is drawn from the tube through the blood vessel wall adjacent the punctures and outward through the tissue tract. A loop in the suture is then secured to close the punctures.

In one particular aspect, a pair of needles having the length of suture therebetween are simultaneously drawn through the blood vessel wall to form the loop. Preferably, at least a portion of the length of suture extending between the pair of needles passes through the guide body and is disposed outside the patient during introduction of the device. The length of suture is then pulled back through guide body during the drawing step. In one aspect, the needle is prevented from being deployed during the introducing step. In a further aspect, the sleeve is secured relative to the guide body after the rotating step.

In yet another aspect, the introducing step further comprises inserting the flexible tube over a guide wire and advancing the tube over the guide wire until the guide wire exits an exit port in the flexible tube. The tube is then further advanced until the tube is within the blood vessel. The guide wire is then withdrawn from the puncture site so that the guide body may be introduced into the tissue tract. In still another aspect, the suturing device is positioned by observing blood flow from a marker lumen in the guide body having a side or marker port between the flexible tube and the distal end of the guide body. In another aspect, the suturing device is withdrawn from the puncture site prior to securing the loop.

DETAILED DESCRIPTION OF THE SPECIFIC EMBODIMENTS

Figure 1:
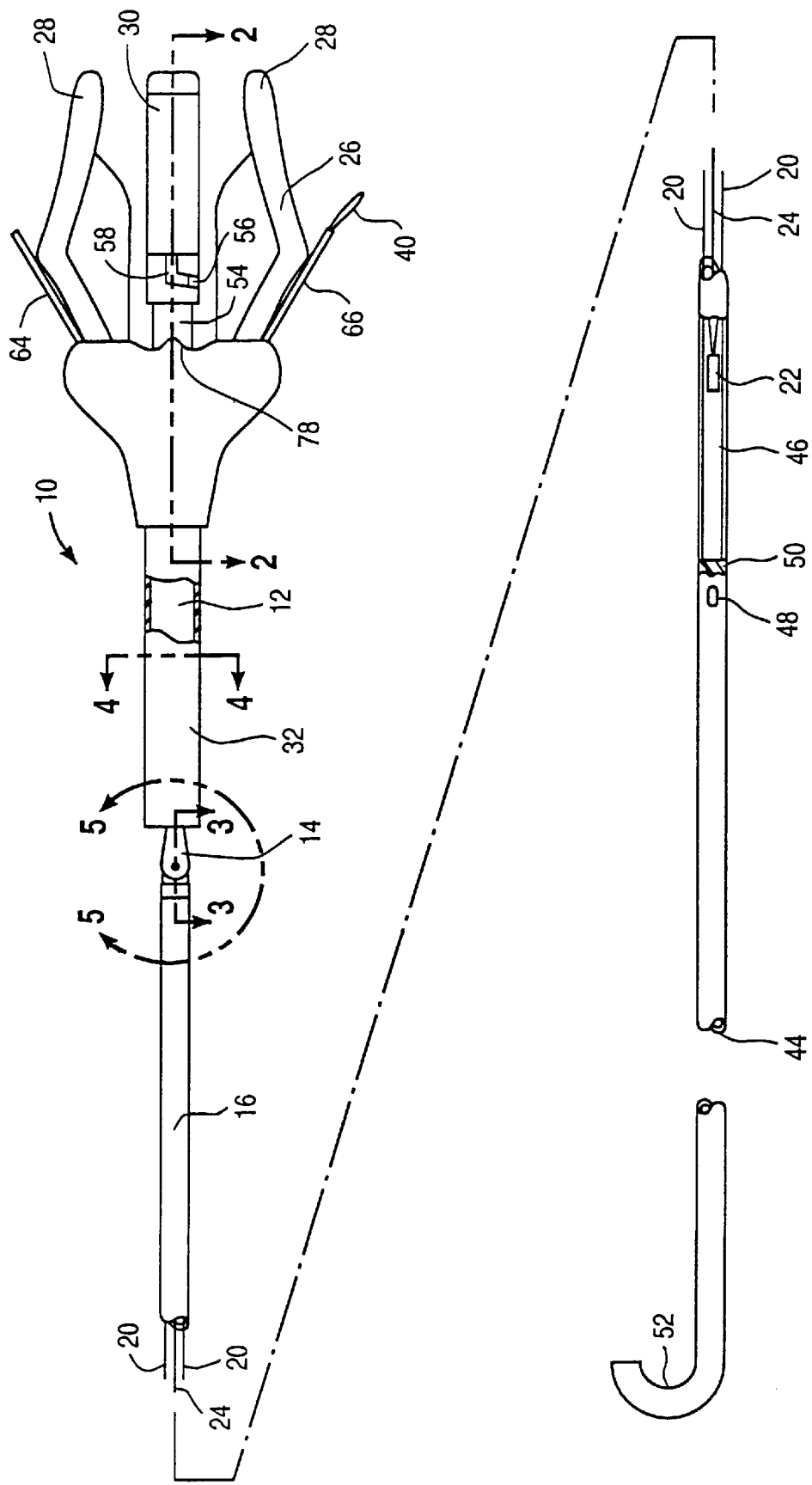
FIG. 1 is a side view of an exemplary suturing device constructed in accordance with the principles of the present invention.

Referring to FIG. 1, a suturing device 10 constructed in accordance with the principles of the present invention will be described. The suturing device 10 comprises a guide body 12, a needle guide 14 secured to a distal end of the guide body 12, and a flexible tube 16 secured to a distal end of the needle guide 14. A pair of needles 20 are mounted with their distal ends in a holder 22 attached to a reciprocatable shaft 24. A handle assembly 26 is attached to a proximal end of the guide body 12 and includes a pair of finger tabs 28 and a handle 30. The handle 30 is attached to a proximal end of the shaft 24 and can be pulled proximally in order to draw the needles 20 from the tube 16, through the needle guide 14 and into the guide body 12, as will be describe in more detail hereinafter.

Rotatably received over the guide body 12 is a sleeve 32. As will be described in greater detail hereinafter, the sleeve 32 may be rotated to facilitate introduction of the suturing device 10 to a puncture site. The sleeve 32 will be sized to be introducible through a percutaneous tissue tract leading to a vascular puncture. In the case of percutaneous punctures made to a patient's femoral artery in the drawing, the sleeve 32 will typically have a diameter in the range from 3 mm to 15 mm, preferably from 7 mm to 10 mm, and length generally in the range from 30 mm to 100 mm, preferably from 50 mm to 75 mm. The sleeve 32 will usually be inflexible, preferably being formed at least partially from metal or a hard plastic material.

Figure 4:
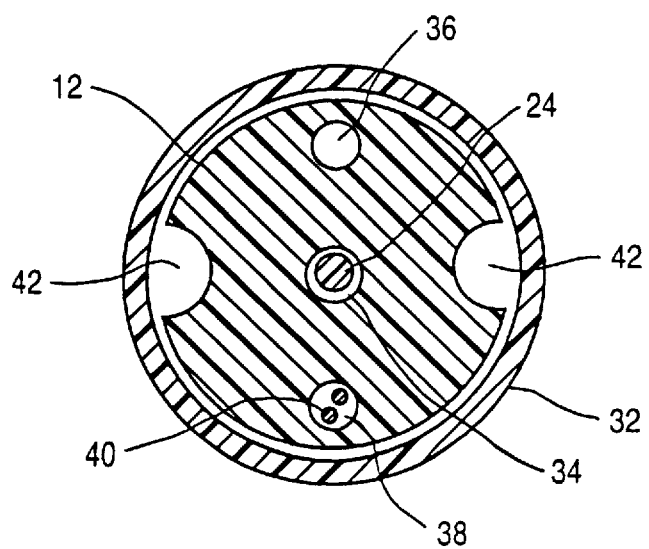
FIG. 4 is a cross-sectional view of the suturing device of FIG. 1 taken along line 4—4 in FIG. 1.

As best shown in FIG. 4, the guide body 12 will define one or more axial lumens or channels therein. A central axial lumen 34 is provided for slidably receiving the shaft 24. The guide body 12 further includes a blood detection lumen 36 and a suture lumen 38 that pass therethrough. The blood detection lumen 36 is provided for receiving blood from the vessel to assist in positioning of the suturing device 10, and the suture lumen 38 is provided for receiving two ends of a length of suture 40 which are attached to the pair of needles 20 as described in greater detail hereinafter. A pair of needle receiving channels 42 are provided for receiving the needles 20 upon reciprocation of the shaft 24.

Referring back to FIG. 1, the flexible tube 16 will be formed from a flexible plastic material, typically from polytetrafluorethylene (PTFE), fluorinated ethylene propylene (FEP), polyethylene, polyester, polyether block amide, and the like. The tube 16 will generally be circular in cross-sectional geometry and will include a guide wire lumen 44 and a central lumen 46 for holding the holder 22 and needles 20. The tube 16 further includes a guide wire exit port 48 for allowing a guide wire that is advanced proximally through the guide wire lumen 44 to exit from the side of the tube 16. The flexible tube 16 will preferably have a diameter in the range from about 2 mm (6F) to 10 mm (30F), more preferably from 2.3 mm (7F) to 4.3 mm (13F). The length of the tube 16 will typically be in the range from 200 mm to 400 mm, preferably from 280 mm to 350 mm. The guide wire exit port 40 will usually be located about 50 mm to 200 mm from the distal end of the needle guide 14. Optionally, the tube 16 may be provided with a distal J-tip 52 for atraumatic tracking through diseased vessels.

A plug 50 is provided to separate the guide wire lumen 44 from the central lumen 46 and is angled in the guide wire lumen 44 to assist in directing the proximally advancing guide wire through the exit port 48. The exit port 48 allows the suturing device 10 to be introduced into a blood vessel in a "monorail" fashion so that only a distal portion of the tube 16 is tracked over the guide wire. In this manner, the profile of the suturing device 10 (and particularly the profile of the needle guide 14 and guide body 12) may be reduced. Reduction in size of the suturing device 10 is advantageous in reducing the amount of trauma during insertion of the device. Further, such a size reduction allows for the sleeve 32 to be included over the guide body 12, thereby eliminating the need for a separate predilator as discussed in greater detail hereinafter.

Figure 2:
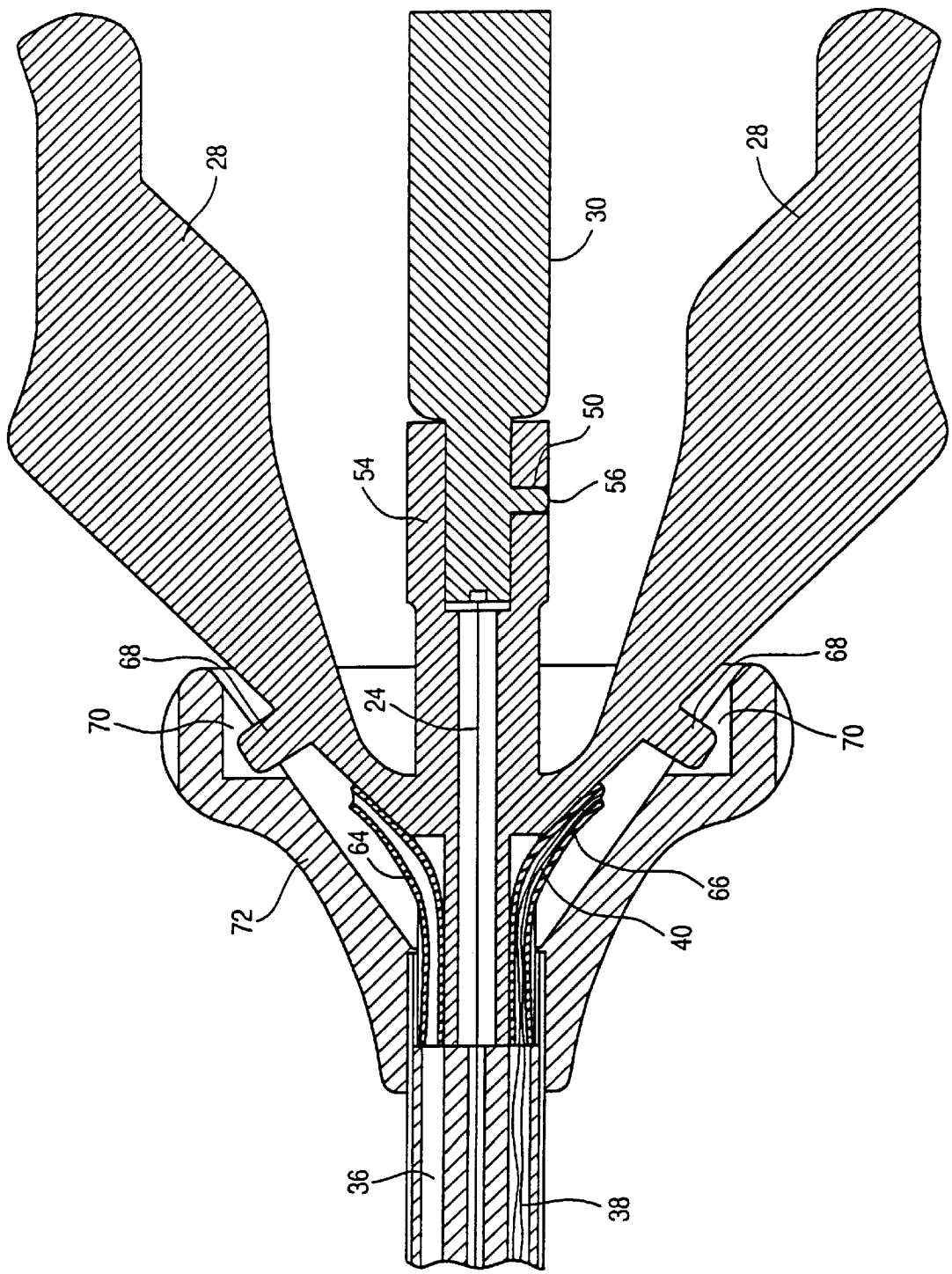
FIG. 2 is a cross-sectional view of the suturing device of FIG. 1 taken along line 2—2.
Figure 6:
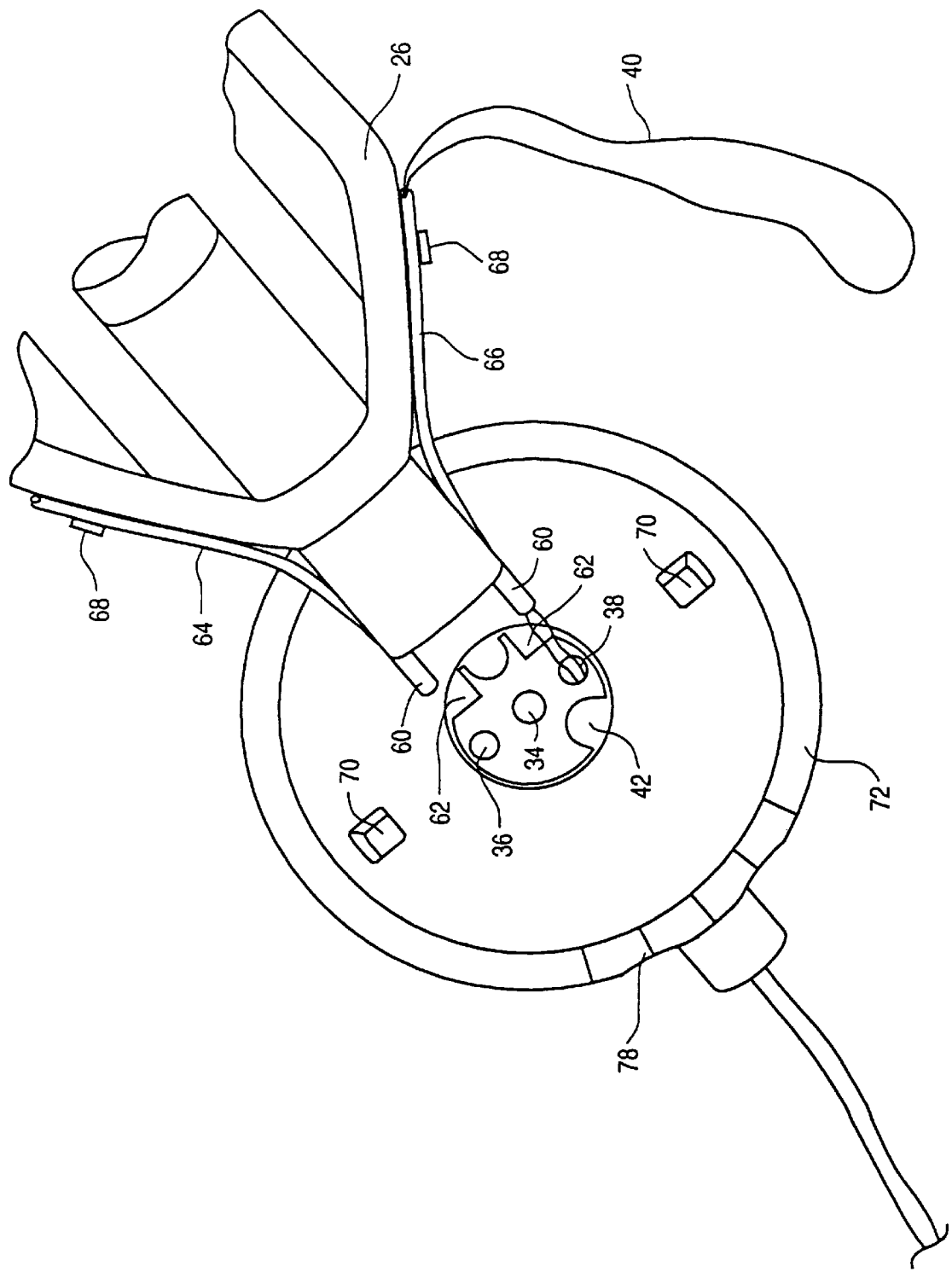
FIG. 6 is a perspective view of the proximal end of the suturing device of FIG. 1 with a handle assembly being shown broken away.

Referring now to FIGS. 2 and 6, construction of the handle assembly 26 and sleeve 32 will be described in greater detail. Integrally formed between the finger tabs 28 is a stem 54 for receiving the handle 30. The handle 30 includes a key 56 that is received into an L-shaped slot 58 in the stem 54. In this manner, the handle 30 may be slid into the stem 54 with the key 56 being received into the L-shaped slot 58. The handle 30 is then rotated in a clockwise direction to secure the handle 30 to the stem 54 and prevent axial translation of the shaft 24. To translate the shaft 24 and deploy the needles 20, the handle 30 is rotated in the counter-clockwise direction so that the key 56 may be pulled from the slot 58. The handle 30 is then proximally translated to deploy the needles 20.

The handle assembly 26 is preferably securely attached to the guide body 12 so that the sleeve 32 may be rotated relative to the guide body 12 when holding the handle assembly 26. The handle assembly 26 may be securely fastened to the guide body 12 by any conventional means known in the art, such as by gluing, molding, and the like, or alternatively, the handle assembly 26 may be formed as an integral part of the guide body 12. One particular way to secure the handle assembly 26 to the guide body 12 is illustrated in FIG. 6 where the handle assembly 26 includes a pair of pins 60 that are received into holes 62 in the guide body 12. Included on the handle assembly 26 are a pair of tubes 64, 66 which are aligned with the blood detection lumen 36 and the suture lumen 38, with the length of suture 40 passing through the tube 66.

Figure 3:
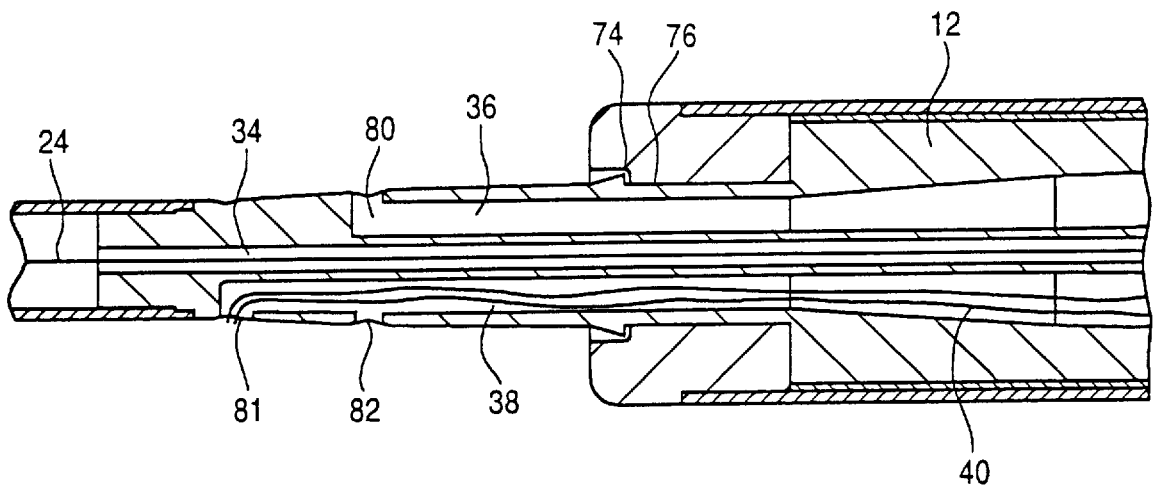
FIG. 3 is a cross-sectional view of the suturing device of FIG. 1 taken along line 3—3 in FIG. 1.

The finger tabs 28 are each provided with a detent 68 for engaging a pair of grooves 70 in a hub 72 of the sleeve 32. The finger tabs 28 will usually be constructed of a resilient material, such as polycarbonate, so that the finger tabs 28 may be pressed together to remove the detents 68 from the grooves 70. Upon removal of the detents 68 from the grooves 70, the sleeve 32 may be rotated relative to the guide body 12 by maintaining a grip on the finger tabs 28 with one hand and rotating the hub 72 with the other hand. As best shown in FIG. 3, the guide body 12 includes a channel 74 about its periphery for receiving an annular collar 76 of the sleeve 32. The collar 76 rests in the channel 74 to allow the sleeve 32 to be freely rotated about the guide body 12 while preventing axial translation of the sleeve 32 relative to the guide body 12. Configuring the sleeve 32 in this manner is advantageous in that the surgeon can quickly introduce the suturing device 10 to the puncture site without the use of a predilator by merely disengaging the handle assembly 26 from the sleeve 32 and rotating the sleeve 32 as it is directed into the tissue tract. A pointer 78 (see FIGS. 1 and 6) may optionally be provided to assist in determining the position of the sleeve 32 relative to the guide body 12.

Referring back to FIG. 3, the lumens 34, 36 and 38 in the guide body 12 will be described in greater detail. The central lumen 34 extends from the flexible tube 16, through the needle guide 14, through the guide body 12 and into the stem 54 of the handle assembly 26. Running the length of the central lumen 34 is the shaft 24. In this way, the handle 30 may be proximally translated to translate the shaft 24 through the central lumen 34 which in turn will translate the needles 20. Running generally in parallel to the central lumen 34 is the blood detection lumen 36 and the suture lumen 38. The blood detection lumen 36 terminates in a marker port 80 in the needle guide 14, while the suture lumen 38 terminates in a suture port 81 and may optionally also include a marker port 82. In this way, the suture lumen 38 may optionally be configured as a "back-up" blood detection lumen (in additional to holding the suture 40) to assist in positioning the suturing device 10 as described hereinafter. Passing through the suture lumen 38 is the length of suture 40. The length of suture 40 is fashioned in the form of the loop with the free ends being attached to the needles 20 (see FIG. 5) and with the looped end passing outside the suturing device 10 through the tube 66 (see FIG. 1). Such a configuration facilitates management of the length of suture 40 during insertion of the suturing device 10 to a puncture site and during proximal translation of the needles 20 to suture close the blood vessel. As the needles 20 are proximally advanced through the guide body 12, the length of suture 40 is drawn distally through the blood detection lumen 38 where it is completely removed from the lumen 38 upon full deployment of the needles 20. In this manner, the blood vessel may be sutured closed after deployment of the needles 20 by merely removing the ends of the suture 40 from the needles 20, withdrawing the suturing device 10 from the puncture site, and tying the free ends of the suture together.

Figure 5:
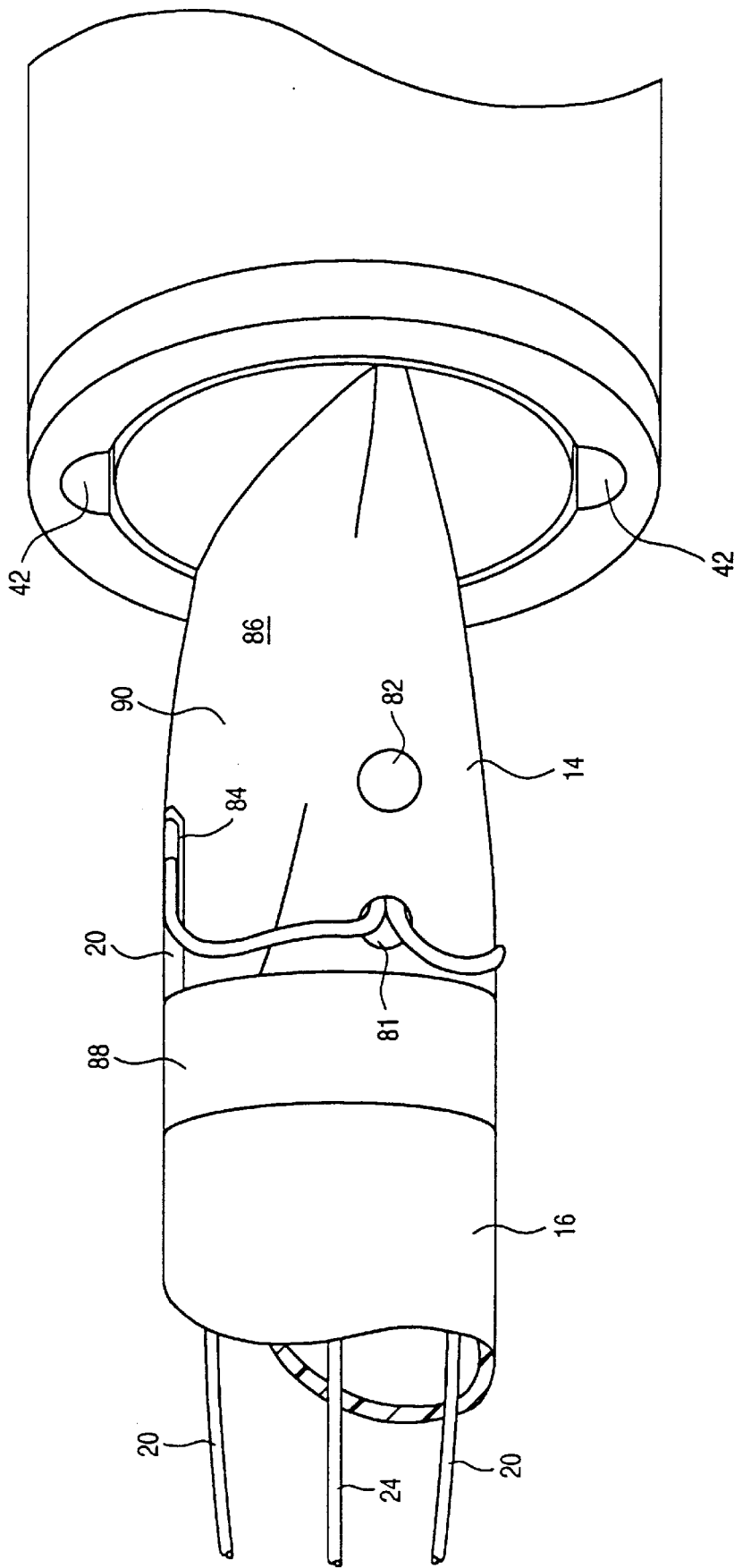
FIG. 5 is a detailed view of a needle guide of the suturing device of FIG. 1 taken along line 5—5 in FIG. 1.

Referring now to FIG. 5, needle guide 14 includes a pair of needle guide channels 84. The needle guide channels 84 serve to house the sharpened ends of the needles 20 during insertion of the needle guide 14 into the blood vessel and also serve as guides to direct the needles 20 toward the needle receiving channels 42 in the guide body during suturing of the blood vessel. The channels 84 are formed in a radially diverging pattern so that the needles 20 passing through the guide 14 will diverge as they pass through tissue over a tissue receiving region 86 at the proximal portion of the guide 14. A retaining band 88 is placed over the distal end of the needle guide channels 84 to retain the needles 20 as they pass therethrough. The retaining band 88 may also be used to secure the proximal end of the flexible tube 16. The needle guide 14 will have a generally circular periphery at its distal end adjacent the retaining band 88. The periphery, however, makes a transition to the tissue receiving region 86 which is generally elliptical in geometry. By providing an elliptical profile at the tissue receiving region 86, the tissue surrounding the puncture to be closed will be disposed to provide a better target for the needles 20 being passed therethrough. In particular, the needles 20 are oriented to pass over the major surfaces 90 of the elliptical tissue receiving region 86. Since the tissue will be partially closed together at this portion of the elliptical region (compared to a circular opening), it will be easier for the needles 20 to find target tissue and become firmly anchored. Preferably, the total peripheral distance over the needle guide 14 will not vary, with only the shape changing. By providing such a constant peripheral distance, hemostasis is maintained as the device is advanced and the tendency to tear or otherwise damage the tissue surrounding the puncture will be reduced. The elliptical configuration of the tissue receiving region 86 is further advantageous in that the needle trajectory angle relative to the guide body 12 is reduced, which in turn reduces the necessary diameter of the sleeve 32. As the needles 20 pass through the tissue, they are received into the needle receiving channels 42 in the guide body 12 where they exit into the hub 72 (see FIG. 6).

Referring to FIGS. 1 and 3, use of the tubes 64 and 66 will be described in greater detail. When the suturing device is introduced into a blood vessel so that the marker port 80 lies within the blood vessel lumen (and is thus exposed to blood pressure), blood will appear at the open end of tube 64 indicating proper positioning of the device. Tube 66 is provided to facilitate management of the suture 40 as previously described. If the market port 82 is included, blood will usually appear at the open end of tube 66 when the device is properly positioned. In this way, the tube 66 serves as a "back-up" indicator in the event that no blood appears in the tube 64 (e.g. in the event that the lumen 36 becomes clogged).

Referring now to FIGS. 7–13, use of the suturing device 10 for closing a vascular puncture P will be described. The vascular puncture P is formed in the wall of a blood vessel BV which is located at the distal end of a tissue tract TT by the Seldinger technique. An introducer sheath I is placed over a guide wire GW passing percutaneously beneath the patient's skin S. The situation illustrated in FIG. 7 will be typical of the end of a wide variety of interventional and/or diagnostic procedures, including angiography, ultrasonic imaging, angioplasty, atherectomy, intravascular drug delivery, and the like. It is desirable that the introducer sheath I be removed and the vascular puncture be closed and sealed.

Figure 7:
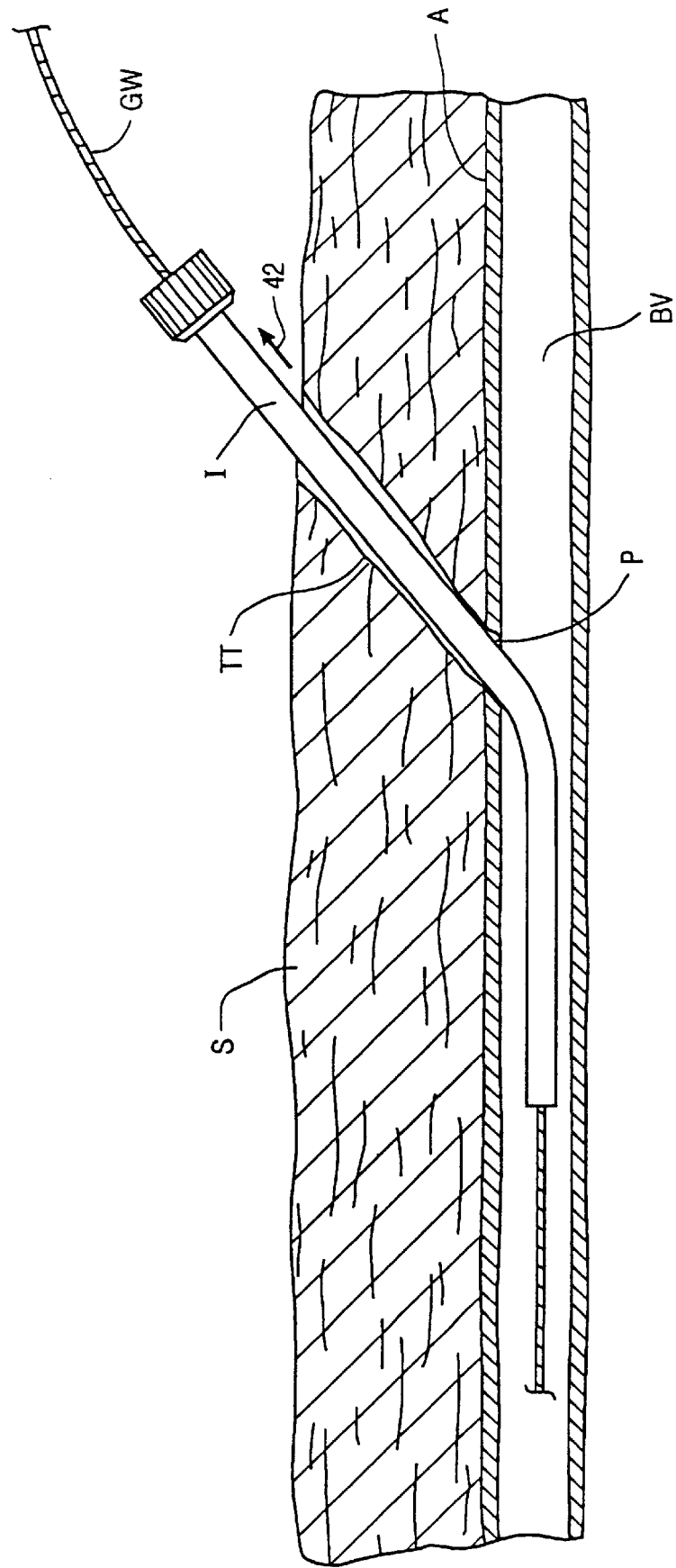
FIGS. 7–13 illustrate use of the suturing device of FIG. 1 in performing a vascular suturing procedure according to the method of the present invention.
Figure 8:
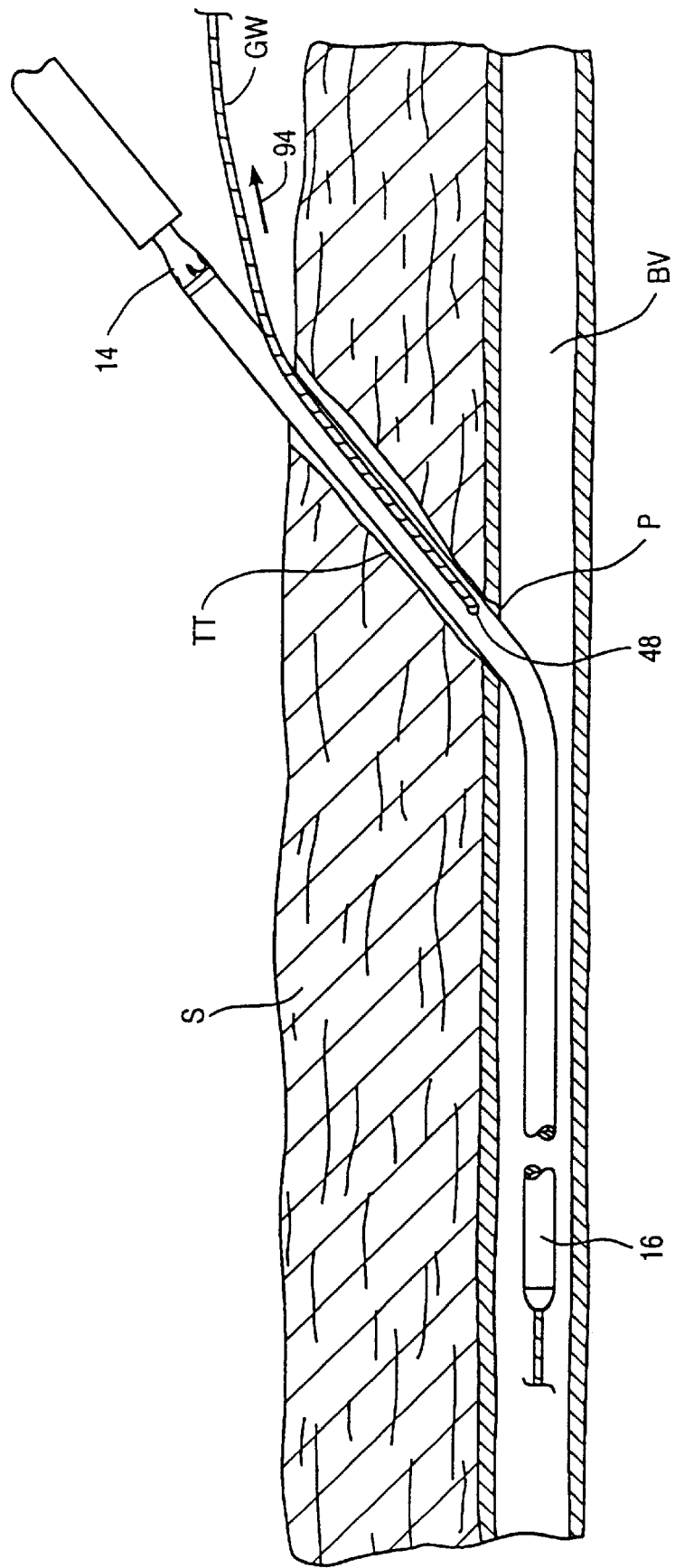

Referring now to FIGS. 7 and 8, the method of the invention begins by withdrawing the introducer sheath I from the puncture P by sliding the introducer I over the guide wire GW as shown by arrow 92. As shown in FIG. 8, the suturing device 10 is then introduced over the guide wire GW by passing the guide wire GW proximally through the flexible tube 16 until the guide wire GW exits the exit port 48. The tube 16 is then further advanced over the guide wire GW until the needle guide 14 is about to enter the tissue tract TT and preferably before the exit port 48 enters the blood vessel BV as shown. At this point, the guide wire GW is pulled from the tube 16 and is withdrawn from the puncture P as indicated by arrow 94. In this manner, the guide wire GW is removed from the puncture P prior to introduction of the needle guide 14 and the guide body 12.

Figure 9:
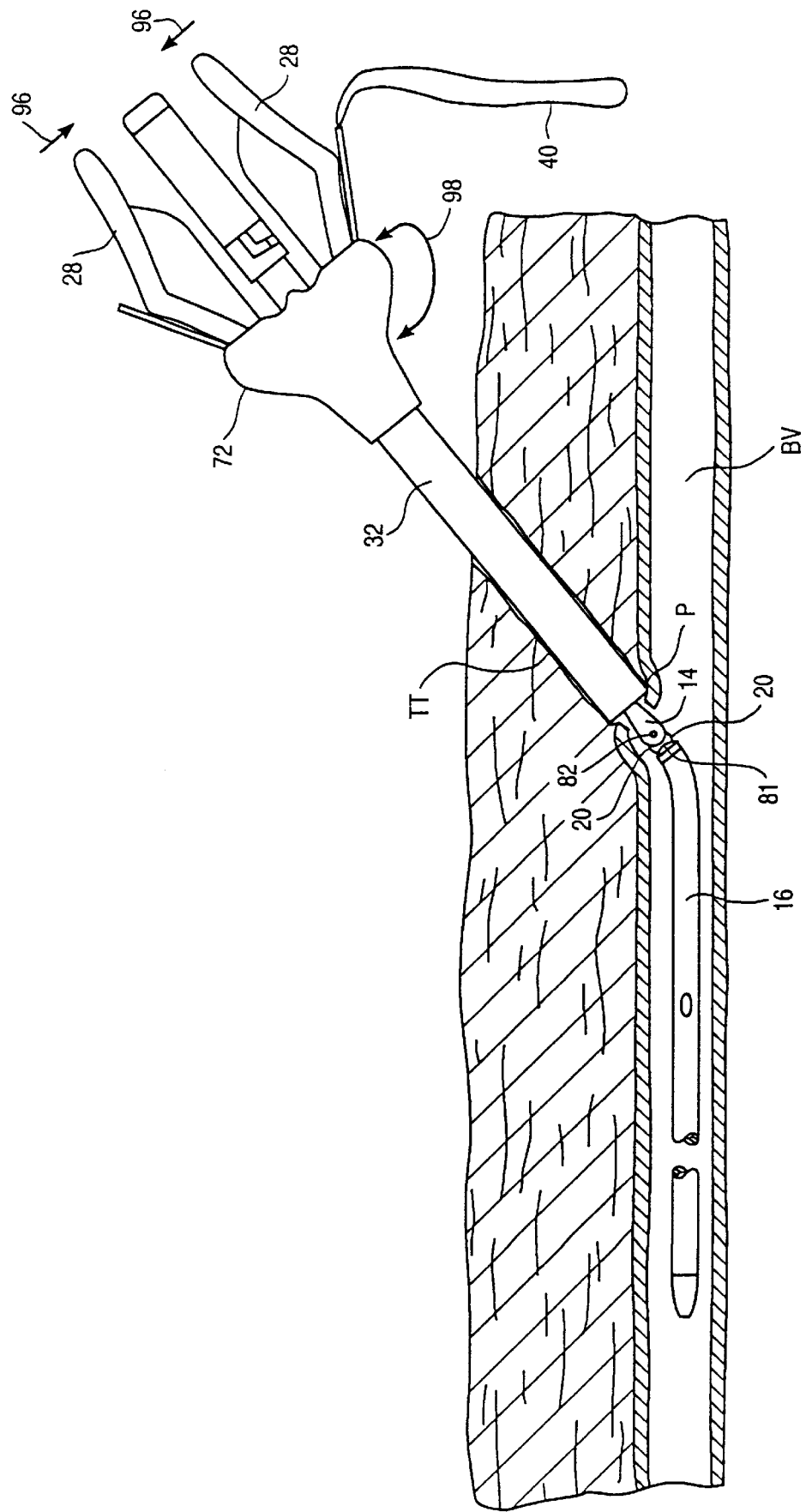

Introduction of the needle guide 14 into the blood vessel BV is illustrated in FIG. 9. With the guide wire GW removed from the puncture P, the finger tabs 28 are grasped with one hand while the hub 72 is grasped with the other hand. The finger tabs 28 are pressed together as indicated by arrows 96 so that the sleeve 32 may be rotated back and forth as indicated by arrow 98. The suturing device 10 is then further advanced into the blood vessel BV to pass the needle guide 14 through the tissue tract TT. While the needle guide 14 is passing through the tissue tract TT, the sleeve 32 is rotated relative to the guide body 12 to help dilate the tissue tract TT. Such dilation is advantageous in reducing the risk of injury to the blood vessel BV during insertion and positioning of the needle guide 14. Furthermore, by providing the sleeve 32, the use of a separate predilator is eliminated, thereby reducing the time and trauma normally experienced with such predilation procedures.

Device 10 is introduced so that the blood marker ports 80, 82 just enter the blood vessel BV lumen, as illustrated. At that point, the needle guide 14 will be properly positioned in the blood vessel BV, with the needles 20 remaining undeployed within the tube 16.

Figure 10:
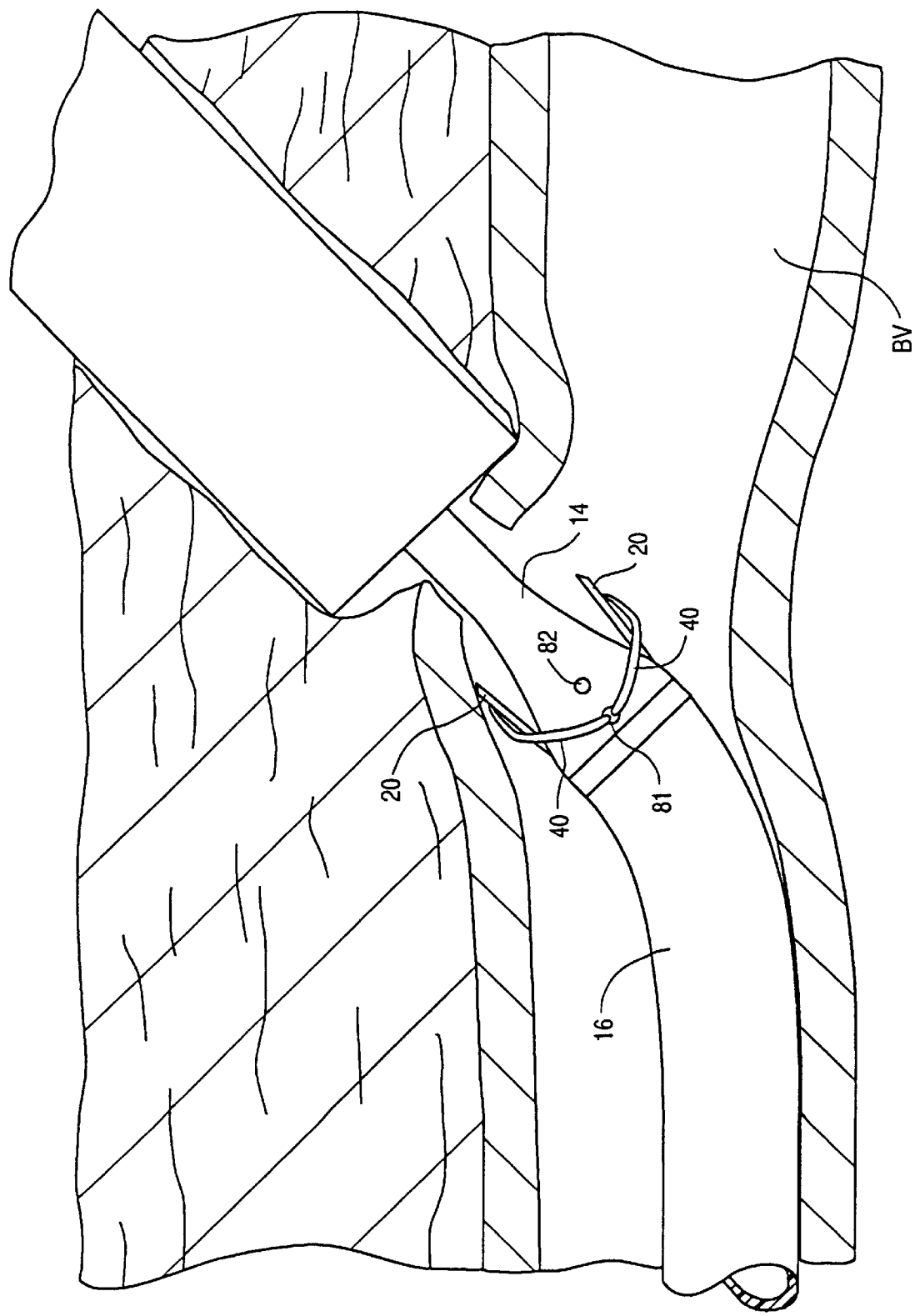
Figure 11:
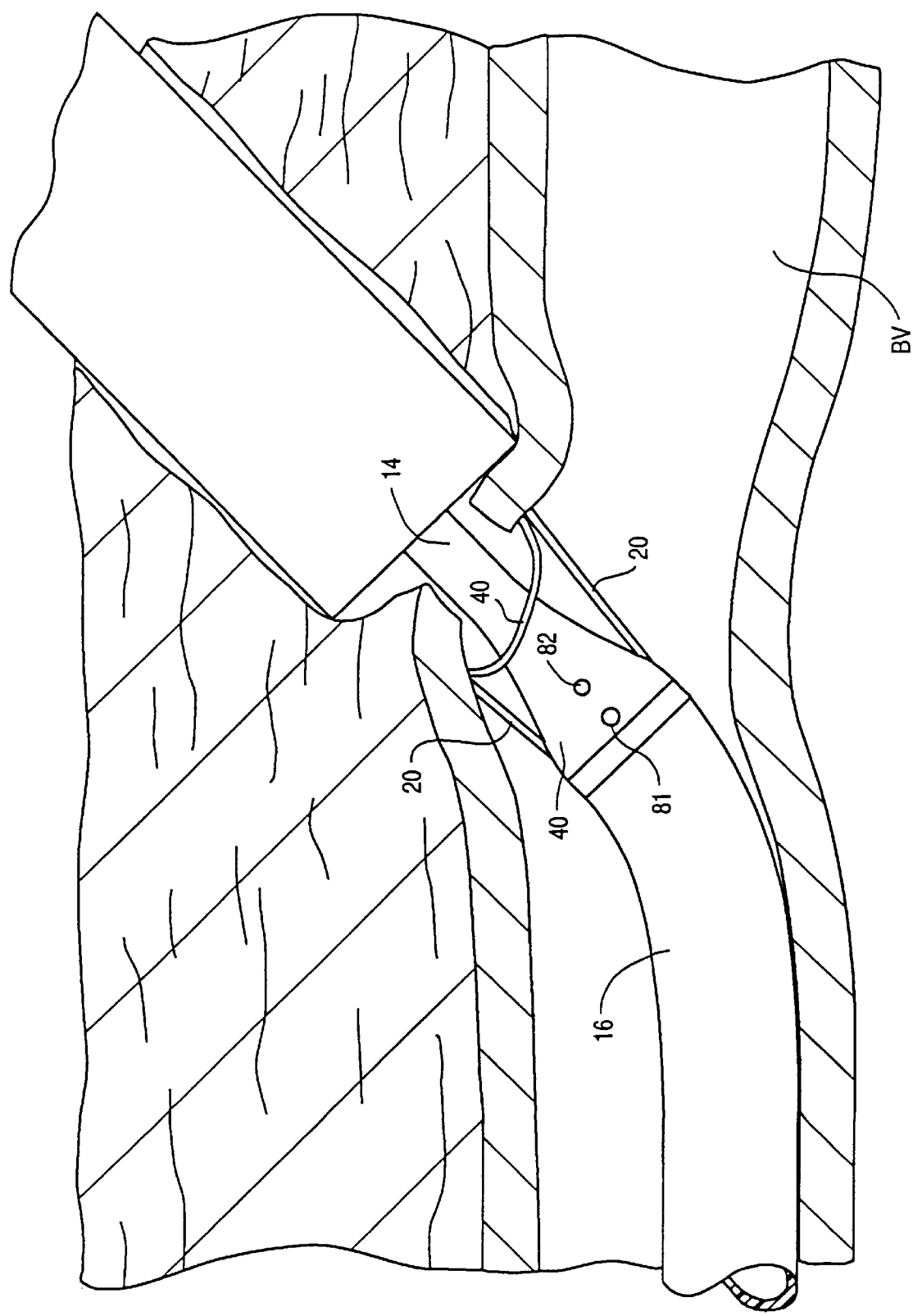
Figure 12:
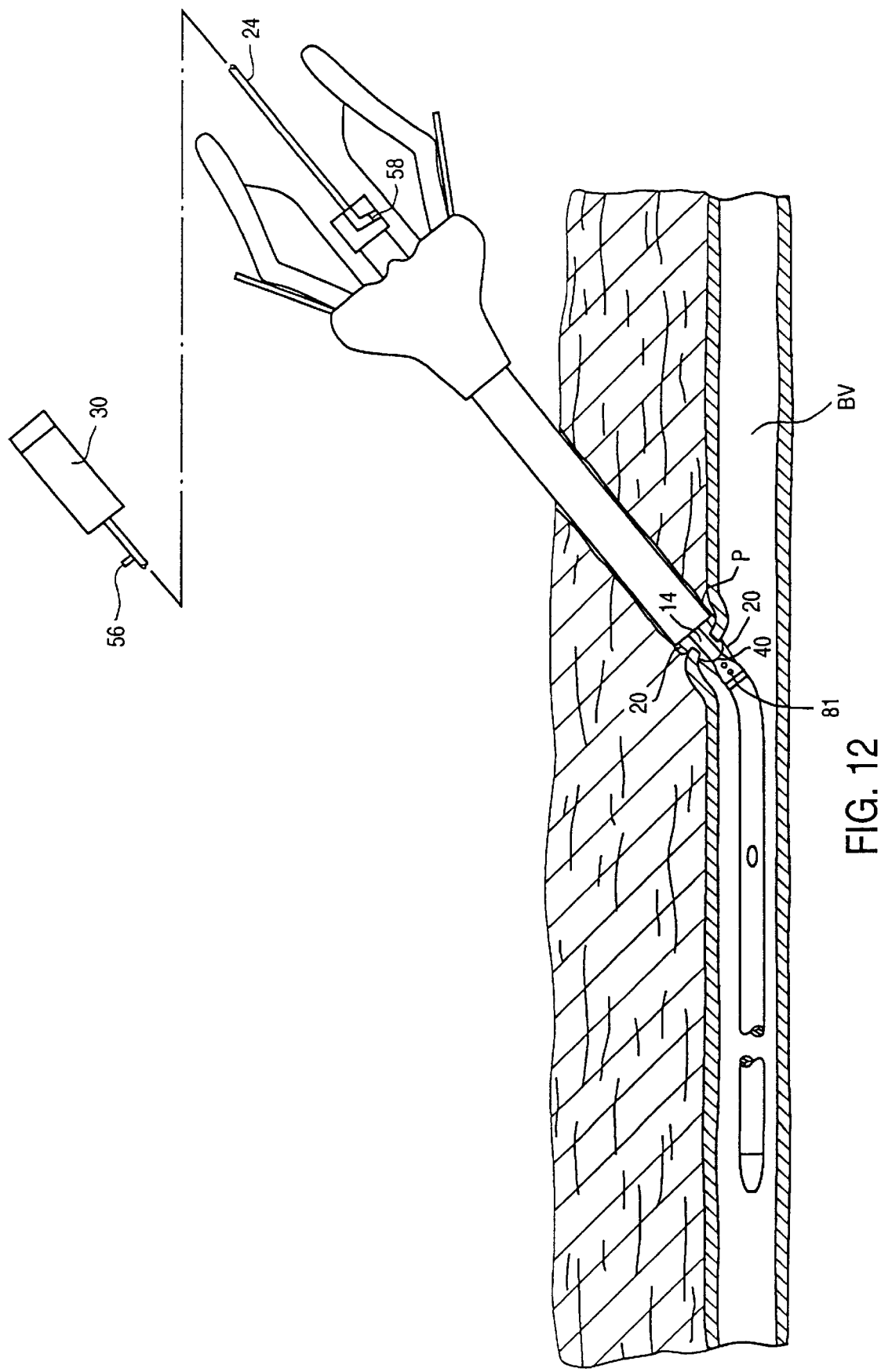

Referring now to FIGS. 10–12, advancement of the needles 20 through the blood vessel wall will be described. To translate the needles 20, the handle 30 is rotated counter-clockwise to disengage the key 56 from the slot 58 and is then proximally translated to proximally translate the shaft 24. As best shown in FIG. 10, the needles 20 will exit from the guide channels 84, pass into the vessel wall, and be directed toward the needle receiving channels 42. As the needles 20 are drawn through the blood vessel wall, the length of suture 40 will be fed through the suture port 81. As best shown in FIGS. 11 and 12, the needles 20 will then be advanced into the receiving channels 42, with the necessary suture being continually fed through the port 81. The needles 20 may then be drawn proximally fully through the guide body 12 until they emerge within the hub 72, with the suture 40 still attached thereto. At that point, the looped portion of the length of suture 40 will be removed from the suture lumen 38 and will be free of the suturing device 10.

The device 10 will then be removed from the tissue tract TT to allow closure of the vascular puncture P. Preferably, preparation for removal will be accomplished by pulling the needles 20 from the holder 22 and then removing the ends of the length of suture 40 from the needles 20. Alternatively, the suture 40 may be removed from the sharpened end of the needles 20, and the needles 20 then reciprocated distally back into the tube 16 in order to permit withdrawal of the suturing device 10. It should be noted that, for safety purposes, the needles 20 can always be retracted distally back into the tube 16 in order to terminate a procedure and removed the suturing device 10.

Figure 13:
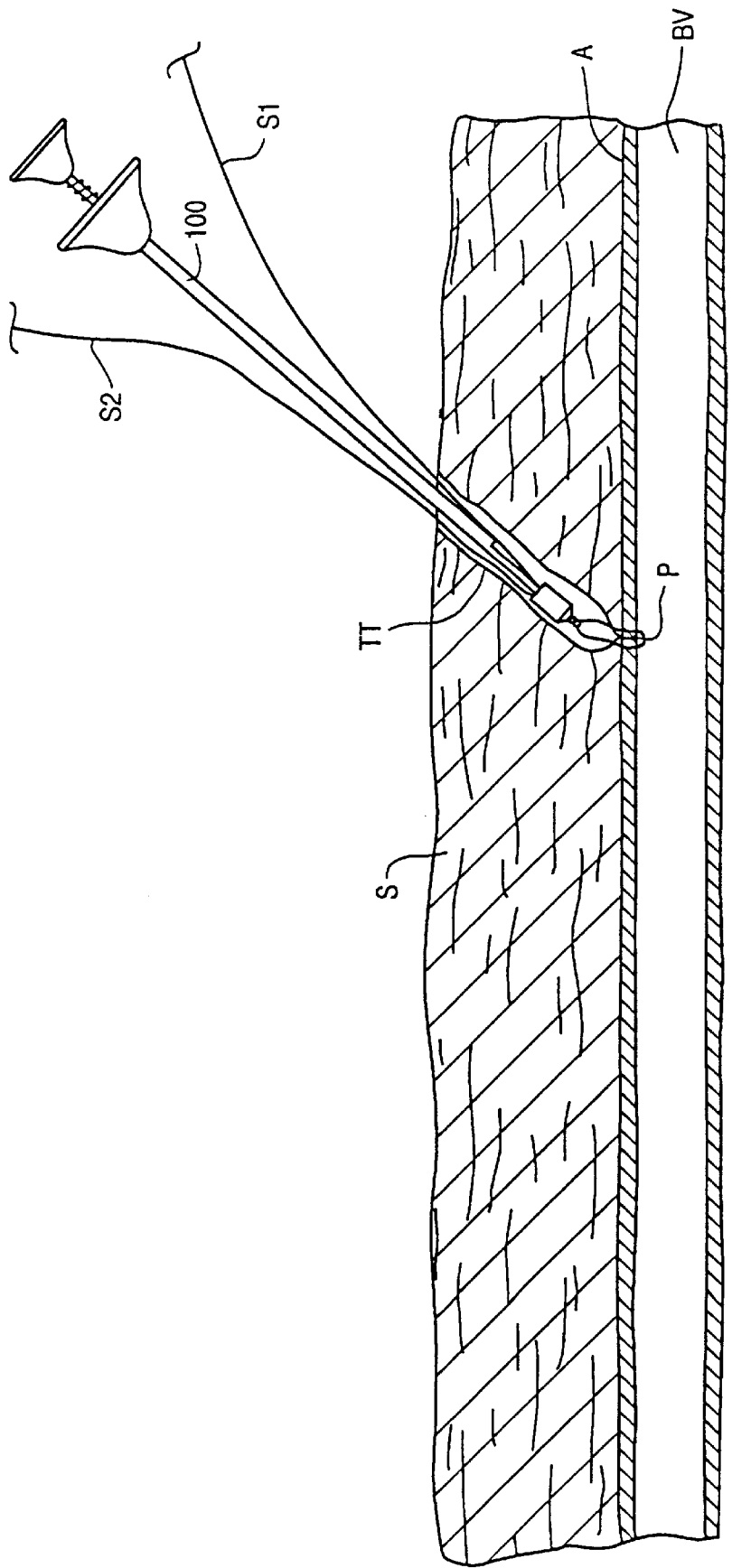

When ready for removal, the suturing device 10 is partially withdrawn from the tissue tract TT and the free ends of the suture S1 and S2 (see FIG. 13) are tied about the tube 16. The entire suturing device 10 is then fully withdrawn with the free ends S1 and S2 remaining tied together. As illustrated in FIG. 13, the knot in the suture 40 is advanced through the tissue tract TT to the adventitial surface A using a knot pusher 100, such as that illustrated in copending application Ser. No. 08/252,310 (attorney docket no. 15508-14) the full disclosure of which is incorporated herein by reference. The suture can also be fastened by using a wide variety of fasteners or other mechanical closure elements.

Although the foregoing invention has been described in some detail by way of illustration and example, for purposes of clarity of understanding, it will be obvious that certain changes and modifications may be practiced within the scope of the appended claims.

What is claimed is:

1. A suturing device comprising:

a guide body;

a translating mechanism which translates at least one needle relative to the guide body;

a rotatable sleeve disposed over at least a distal portion of the guide body, wherein the rotatable sleeve is operably attached to the guide body such that the rotatable sleeve may rotate about the guide body while substantial axial movement of the rotatable sleeve relative to the guide body is prevented.

2. A suturing device as in claim 1, wherein the rotatable sleeve is a rigid cylinder having a length in the range from 30 mm to 200 mm and a diameter in the range from 3 mm to 15 mm.

3. A suturing device as in claim 1, further comprising a flexible tube extending distally from the guide body, wherein the flexible tube includes a proximal end, a distal end, and a guide wire lumen extending proximally from the distal end and terminating in an exit port between the proximal and distal ends.

4. A suturing device as in claim 3, wherein the flexible tube has a length in the range from about 20 cm to 40 cm, and further comprising a side port which is located at about 5 cm to 20 cm from the proximal end.

5. A suturing device as in claim 4, wherein the flexible tube has an outside diameter in the range from about 2 mm to 10 mm.

6. A suturing device as in claim 3, wherein the flexible tube further includes a central lumen extending distally from the proximal end, the central lumen being sized to house the needle.

7. A suturing device as in claim 1, further comprising a stopping mechanism to selectively prevent rotation of the sleeve.

8. A suturing device as in claim 7, wherein the stopping mechanism comprises a handle attached to the guide body, the handle having at least one detent for engaging a groove in the sleeve.

9. A suturing device as in claim 1, further comprising at least one blood detection lumen passing through the guide body.

10. A suturing device as in claim 9, further comprising a suture lumen passing through the guide body, said suture lumen housing a length of suture.

11. A suturing device comprising:
a guide body;
a translating mechanism to translate at least one needle relative to the guide body;
a flexible tube having a proximal end connected to the guide body, a distal end, and a guide wire lumen initiating at the distal end and terminating in a guide wire exit port between the proximal end and the distal end; and
a sleeve rotatably disposed about the guide body.

12. A suturing device as in claim 11, further comprising a handle attached to the guide body, the handle having at least one detent for engaging a groove in the sleeve.

13. A suturing device as in claim 11, wherein the flexible tube has a length in the range from about 20 cm to 40 cm, and wherein the exit port is located at about 5 cm to 20 cm from the proximal end.

14. A suturing device as in claim 11, wherein the flexible tube has an outside diameter in the range from about 2 mm to 10 mm.

15. A suturing device as in claim 11, wherein the flexible tube includes means for directing a proximally advanced guide wire through the exit port.

16. A suturing device as in claim 11, wherein the rotatable sleeve is a rigid cylinder having a length in the range from 30 mm to 200 mm and a diameter in the range from 3 mm to 15 mm.

17. A suturing device as in claim 11, further comprising at least one blood detection lumen passing through the guide body.

18. A suturing device as in claim 17, further comprising a suture lumen passing through the guide body, said suture lumen housing a length of suture.

19. A suturing device comprising:
a guide body having a proximal end, a distal end, and an internal lumen;
a needle guide having a proximal end attached to the distal end of the guide body and a distal end having at least two needle guide channels, said needle guide further including a proximal region and a distal region, wherein the needle guide channels are disposed in the distal region and wherein the proximal region includes a recessed portion for receiving a section of tissue;
a pair of needles;
a length of suture having two ends, with each end attached to one of the needles and with at least a portion of the remaining length of suture passing through the internal lumen of the guide body;
a shaft reciprocatably mounted within the guide body and carrying the needles to reciprocate the needles within the needle guide channels; and
a pair of receiving channels in the guide body which are separate from the internal lumen, wherein the pair of needles are operably connected to the shaft such that reciprocation of the shaft draws the needles into the receiving channels and draws the length of suture from the internal lumen.

20. A suturing device as in claim 19, further comprising a blood detection lumen which is separate from the internal lumen.

21. A method for suturing a puncture site in a blood vessel wall disposed at the distal end of a percutaneous tissue tract, said method comprising:
introducing a suturing device having a guide body and a flexible tube distally extending from the guide body to the puncture site so that the guide body lies within the tissue tract and the flexible tube lies within the blood vessel lumen;
drawing a pair of needles with a length of suture therebetween from the flexible tube through the blood vessel wall adjacent the puncture and outward through the tissue tract, wherein at least a portion of the length of suture extending between the pair of needles passes through a lumen in the guide body and is located outside the patient during the introduction step, wherein the length of suture is pulled back through the guide body lumen during the drawing step, and wherein the needles are received into receiving channels within the guide body which are separate from the lumen; and
securing a loop in the suture to close the punctures.

22. A method as in claim 21, wherein the suturing device includes a sleeve rotatably disposed about the guide body, and further comprising rotating the sleeve relative to the guide body while introducing the guide body into the puncture site.

23. A method as in claim 21, wherein the introducing step further comprises inserting the flexible tube over a guide wire and advancing the tube over the guide wire until the guide wire exits an exit port in the flexible tube.

24. A method as in claim 23, further comprising withdrawing the guide wire from the puncture site prior to introducing the guide body into the tissue tract.

25. A method as in claim 21, further comprising positioning the suturing device by observing blood within a marker lumen in the guide body having a side port between the flexible tube and the distal end of the guide body.

26. A method as in claim 21, further comprising withdrawing the suturing device from the puncture site prior to securing the loop.

27. A method as in claim 21, further comprising inhibiting deployment of the needle during the introducing step.

* * * * *